(12) United States Patent
Evans et al.

(10) Patent No.: US 9,757,190 B2
(45) Date of Patent: Sep. 12, 2017

(54) METHODS OF MANUFACTURING MONOPHASIC ACTION POTENTIAL MAPPING CATHETERS

(71) Applicant: MEDTRONIC ABLATION FRONTIERS LLC, Minneapolis, MN (US)

(72) Inventors: Jon Virgil Evans, Eden Prairie, MN (US); George Wedell Gullickson, Bloomington, MN (US); Mark T. Stewart, Lino Lakes, MN (US)

(73) Assignee: Medtronic Ablation Frontiers LLC, Minneapolis, MN (US)

( * ) Notice: Subject to any disclaimer, the term of this patent is extended or adjusted under 35 U.S.C. 154(b) by 1268 days.

(21) Appl. No.: 13/750,561

(22) Filed: Jan. 25, 2013

(65) Prior Publication Data

US 2014/0047712 A1     Feb. 20, 2014

Related U.S. Application Data

(60) Provisional application No. 61/684,385, filed on Aug. 17, 2012, provisional application No. 61/727,163, filed on Nov. 16, 2012.

(51) Int. Cl.
*A61B 18/14*     (2006.01)
*H01R 43/24*     (2006.01)
(Continued)

(52) U.S. Cl.
CPC .......... *A61B 18/1492* (2013.01); *A61B 5/042* (2013.01); *A61B 18/14* (2013.01);
(Continued)

(58) Field of Classification Search
CPC . H01R 43/24; A61N 1/04–1/06; A61B 5/042; A61B 5/0422; A61B 18/1492; A61B 18/14; A61B 18/18; Y10T 29/49176
See application file for complete search history.

(56) References Cited

U.S. PATENT DOCUMENTS 3,769,984 A    11/1973   Muench
5,230,349 A    7/1993    Langberg
(Continued)

FOREIGN PATENT DOCUMENTS

CN    1935099 A     3/2007
CN    100998500 A   7/2007
(Continued)

*Primary Examiner* — Livius R Cazan
(74) *Attorney, Agent, or Firm* — Christopher & Weisberg, P.A.

(57) ABSTRACT

A method for manufacturing a distal portion of a mapping and/or ablation device with fewer components and manufacturing steps than are required for presently known devices. The method generally includes aligning one or more electrodes and electrode wires within a housing mold, overmolding a biocompatible material over the one or more wires and a portion of each of the one or more electrodes, creating a housing component that integrates a dome component and an insulation component. Alternatively, the method generally includes aligning one or more wires within a housing mold so that at least a portion of each wire protrudes from the mold, overmolding a biocompatible material over the one or more wires, thus creating a housing component that integrates a dome component and insulation component. The protruding wire portions are cleaved off and at least a portion of the housing component is coated with a layer of conductive material.

10 Claims, 6 Drawing Sheets

(51) Int. Cl.
  *A61L 29/02*    (2006.01)
  *A61B 5/042*    (2006.01)
  *A61B 18/18*    (2006.01)
  *H05K 13/00*    (2006.01)
  *A61B 18/00*    (2006.01)

(52) U.S. Cl.
  CPC .............. *A61B 18/18* (2013.01); *A61L 29/02* (2013.01); *H01R 43/24* (2013.01); *H05K 13/0046* (2013.01); *A61B 2018/0016* (2013.01); *A61B 2018/00029* (2013.01); *A61B 2018/00071* (2013.01); *A61B 2018/00083* (2013.01); *A61B 2018/00095* (2013.01); *A61B 2018/00107* (2013.01); *A61B 2018/00351* (2013.01); *A61B 2018/00577* (2013.01); *A61B 2018/00642* (2013.01); *A61B 2018/00839* (2013.01); *A61B 2018/1407* (2013.01); *A61B 2018/147* (2013.01); *A61B 2018/1435* (2013.01); *A61B 2018/1467* (2013.01); *A61B 2018/1497* (2013.01); *Y10T 29/49172* (2015.01); *Y10T 29/49176* (2015.01)

(56) References Cited

U.S. PATENT DOCUMENTS

| | | |
|---|---|---|
| 5,833,714 A | 11/1998 | Loeb |
| 5,849,031 A | 12/1998 | Martinez et al. |
| 7,174,219 B2 | 2/2007 | Wahlstrand et al. |
| 2004/0064175 A1 | 4/2004 | Lessar et al. |
| 2010/0261990 A1 | 10/2010 | Gillis et al. |
| 2010/0305675 A1 | 12/2010 | Laske et al. |
| 2011/0028820 A1 | 2/2011 | Lau et al. |
| 2011/0130816 A1* | 6/2011 | Howard ............... A61N 1/0534 607/116 |

FOREIGN PATENT DOCUMENTS

| | | |
|---|---|---|
| CN | 101999931 B | 11/2012 |
| CN | 102125460 B | 11/2012 |
| EP | 0428812 B1 | 3/1995 |
| WO | 0033734 A1 | 6/2000 |

\* cited by examiner

METHODS OF MANUFACTURING MONOPHASIC ACTION POTENTIAL MAPPING CATHETERS

CROSS-REFERENCE TO RELATED APPLICATION

This application is related to and claims priority to U.S. Provisional Patent Application Ser. No. 61/684,385, filed Aug. 17, 2012, entitled MONOPHASIC ACTION POTENTIAL CATHETER DESIGN, and is related to and claims priority to U.S. Provisional Patent Application Ser. No. 61/727,163, filed Nov. 16, 2012, entitled MONO-PHASIC ACTION POTENTIAL ELECTROGRAM CATHETER, the entirety of both of which is incorporated herein by reference.

STATEMENT REGARDING FEDERALLY SPONSORED RESEARCH OR DEVELOPMENT n/a

FIELD OF THE INVENTION

The present invention relates to an improved method of manufacturing mapping and ablation devices.

BACKGROUND OF THE INVENTION

Medical procedures are available for treatment of a variety of cardiovascular conditions, such as cardiac arrhythmias, including atrial fibrillation, and other irregularities in the transmission of electrical impulses through the heart. As an alternative to open-heart surgery, many medical procedures are performed using minimally invasive surgical or transvenous intracardiac catheter techniques, where one or more slender implements are inserted through one or more small incisions into a patient's body. Such procedures may involve the use of catheters or probes having multiple sensors, electrodes, or other measurement and treatment components to treat the diseased area of the heart, vasculature, or other tissue. Minimally-invasive devices are desirable for various medical and surgical applications because they allow for shorter patient recovery times compared to surgery, and for precise treatment of localized discrete tissues that are otherwise difficult to access. For example, catheters may be easily inserted and navigated through the blood vessels and arteries, allowing less-invasive access to areas of the body with relatively little trauma, while other minimally-invasive probes or instruments may be inserted into small openings and directed through targeted anatomy without significant impact or disruption to surrounding tissue.

One such example of a minimally invasive therapy involves the treatment of cardiac arrhythmias or irregular heartbeats in which physicians employ specialized cardiac assessment and treatment devices, such as a mapping and/or ablation catheter, to gain access to interior regions of a patient's body. Such devices may include tip electrodes or other ablating elements to create lesions or other anatomical effects that disrupt or block electrical pathways through the targeted tissue. In the treatment of cardiac arrhythmias, a specific area of cardiac tissue having aberrant electrical activity (e.g. focal trigger, slow conduction, excessively rapid repolarization, fractionated electrogram, etc.) is typically identified first before subsequent treatment.

MAP recording devices, ablation devices, and combination mapping and ablation devices may include many individual parts, which makes manufacturing difficult and expensive. For example, one device had a tip electrode design that included spherical balls welded or formed at the end of round Platinum rod stock. Early methods of manufacture used to produce these devices proved inconsistent and produced an electrode sphere that was not completely round. As a result, it was difficult to properly seat the electrodes in the dome component at the distal portion of the device. The electrodes also could become misaligned within the dome component when the electrode sphere was welded to a wire, because the wire was so easily attached to a point eccentric to the axis of the electrode. Further, such devices are expensive to manufacture, due in large part to the use of separate costly components. The use of multiple components further makes breakage during use more likely, which may result in injury to the patient.

To provide more effective and efficient methods of manufacturing mapping devices and methods of medical treatments, it is thus desirable to minimize the number of individual components used to manufacture a mapping and/or ablation device and to optimize the functionality of each component used.

SUMMARY OF THE INVENTION

The present invention advantageously provides a method for manufacturing a distal portion of a mapping and/or ablation device with fewer components and manufacturing steps than are required for presently known devices. In one embodiment, the method may include providing one or more wires composed of an electrically conductive material, each wire having a longitudinal axis, providing a housing mold having a first end and a second end, aligning the one or more wires within the housing mold so that at least a portion of each of the one or more wires protrudes from both the first end and second end of the housing mold, and introducing a biocompatible material into the housing mold and letting the material cure, so as to create a housing component overmolded onto the one or more wires. The one or more wires may be securely affixed within the housing component. The housing component may define a distal portion and a proximal portion, and the distal portion may define one or more rounded portions disposed on the distal portion, for example, three or more rounded portions. The rounded portions may be substantially hemispherical, and may be positioned on the distal portion of the housing component in a radially symmetrical pattern. Further, the protruding portion of each of the one or more wires may protrude from an exit point on each of the one or more rounded portions. The protruding portion of each of the one or more wires may then be cleaved off so that surface of the one or more rounded portions and the cleaved portion of each of the one or more wires are substantially coplanar. The surface of each of the one or more rounded portions may then be coated with a layer of conductive material, for example, platinum-iridium. The layer of conductive material on each hemispherical portion may be in communication with one of the at least one electrode wire.

In a second embodiment, the method may include providing an electrode and an electrode wire, the electrode wire having a longitudinal axis, a proximal end, and a distal end, affixing the electrode wire to the electrode, providing a housing component mold defining a first end and a second end, aligning the electrode and electrode wire within the housing component mold such that at least a portion of the electrode protrudes from the second end of the housing component mold and at least a portion of the electrode wire protrudes from the first end of the housing component mold, introducing a biocompatible material into the housing component mold, allowing the biocompatible material to set, creating a housing component, and removing the housing component from the housing component mold, the housing component both rigidly encapsulating and insulating the electrode. The electrode may define a rounded head portion, a neck portion, and a shoulder portion, and the shoulder portion may define at least one flat surface. The electrode may further defines a distal portion and a proximal portion, and the at least one flat surface of the shoulder portion may include a flat surface at the proximal portion of the electrode. Further, the neck portion has a diameter that is less than the diameter of each of the rounded head portion and the shoulder portion. The distal end of the electrode wire may be affixed to the flat surface at the proximal portion of the electrode. Alternatively, the electrode may further define a longitudinal axis and a recess that is coaxial with the longitudinal axis of the electrode, and the electrode wire may be affixed to the electrode by inserting the distal end of the electrode wire into the recess in the electrode, so that the longitudinal axis of the electrode and the longitudinal axis of the electrode wire are substantially coaxial. The biocompatible material may be polyetheretherketone (PEEK), polyurethane, or polyetherimide.

In a third embodiment, the method may include providing a wire composed of an electrically conductive material, the wire defining a longitudinal axis, a distal portion, and a proximal portion, providing a housing mold having a first end and a second end, aligning the wire within the housing mold so that the distal portion of the wire protrudes from the first end of the housing mold and the proximal portion of the wire protrudes from the second end of the housing mold, overmolding the wire with a biocompatible material, removing a housing component from the housing mold, the wire being securely affixed within the housing component, removing the protruding distal portion of the wire, and applying a layer of conductive material to at least a portion of the housing component, such that the wire within the housing component is in communication with the layer of conductive material. The method may further include aligning a pull wire within the housing mold, the pull wire having a proximal portion, such that the proximal portion of the pull wire protrudes from the second end of the housing mold.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
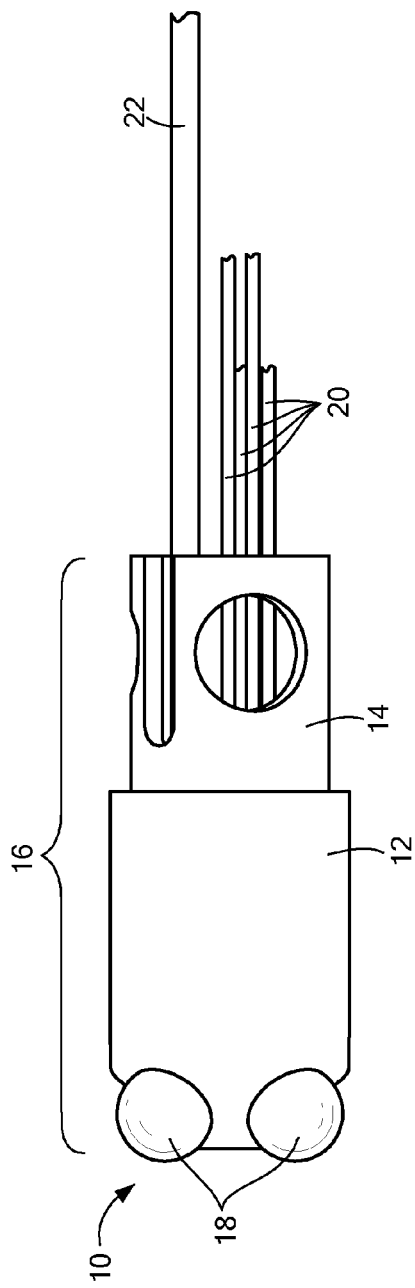
FIG. 1 shows a distal portion of a medical device having a dome component portion and insulation component portion combined into a housing component.

Referring now to FIG. 1, a distal portion 10 of a medical device (for example, a MAP recording device) with combined dome component 12 and insulation component 14 is shown. Currently known MAP recording devices typically have a distal portion that includes a separate dome component and an insulation component. During manufacture, electrodes are coupled to the dome component, which is then bonded to the insulation component. The insulation component is then fused to the catheter tip tubing. However, these components may become dislodged, the separated parts quickly becoming thrombogenic and, thus, hazardous to the patient. Further, using multiple components may be very expensive, not just in material costs, but also because of manufacturing difficulty (for example, due to the small size of individual components) and assembly time. Unlike currently known recording devices, a device having a distal portion as shown in FIG. 1 is less expensive, easier to manufacture, and improves patient safety.

Continuing to refer to FIG. 1, the distal portion 10 of a medical device includes a single housing component 16 that is substantially analogous to the separate dome component 12 and insulation component 14 of currently known devices. The entire housing component 16 may be composed of a biocompatible material such as polyetheretherketone (PEEK), polyurethane, or polyetherimide. The housing component 16 may therefore be manufactured in a single, less intricate process that reduces cost, increases ease of manufacture, and increases patient safety.

Figure 2:
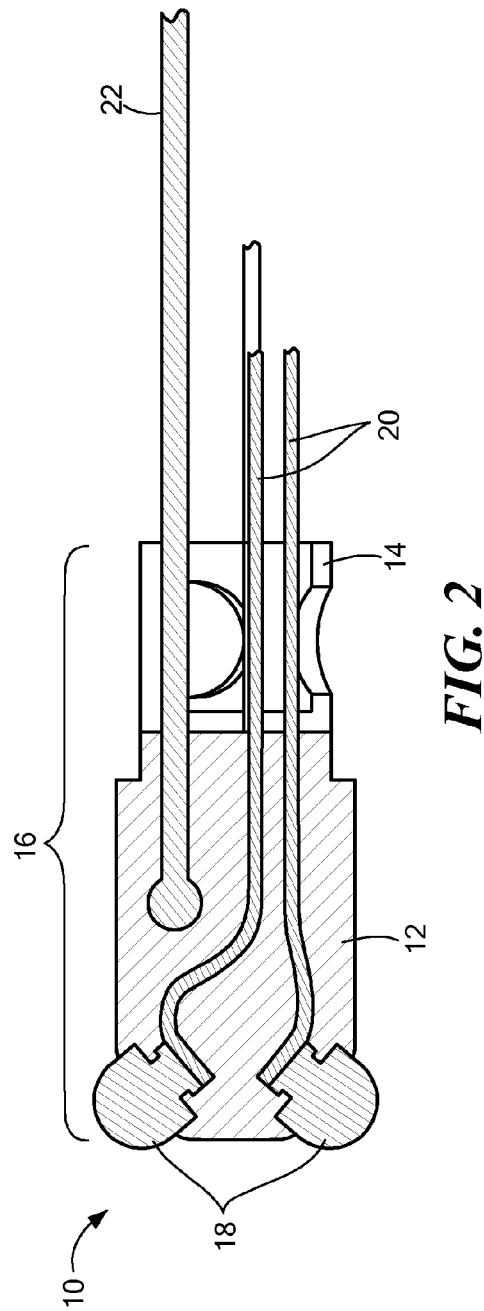
FIG. 2 shows a cross-sectional view of a distal portion of a medical device having a housing component that is overmolded onto the tip electrodes, electrical wires, and pull wire.

Referring now to FIG. 2, a cross-sectional view of a distal portion of a medical device (for example, a MAP recording device) having a housing component that is overmolded onto the tip electrodes, electrical wires, and pull wire is shown. The cross-sectional view of FIG. 2 shows an exemplary alignment of components within a housing component 16 shown in FIG. 1. The medical device distal portion 10 shown in FIG. 2 includes a single housing component 16 that is substantially analogous to the separate dome component 12 and insulation component 14 of currently known devices. That is, the housing component 16 may house electrodes and electrode wires like a conventional dome component, but may also insulate the electrodes from the rest of the catheter body when the distal portion is coupled to a catheter. The housing component 16 of FIG. 2 may be overmolded (either in a single shot or multiple shots) onto the tip electrodes 18, electrical wires 20, pull wire 22, and/or other internal or external device components. The benefit of overmolding is that it may allow for a strong bond, without the use of adhesives, between the housing component and the other device components that is maintained when the device is in use. A further benefit of overmolding the housing compartment onto the electrodes is that the electrodes will not need to be meticulously seated into corresponding recesses in the housing component. As shown and discussed in FIGS. 4 and 5, properly positioning an electrode within a device distal portion housing may be very difficult. A still further benefit of overmolding is that the pull wire 22 will be anchored within the housing component 16, thereby reducing or eliminating the need for additional pull wire anchoring mechanisms. A medical device distal portion 10 manufactured by overmolding a housing component 16 onto other device components may include any number and configuration of electrodes 18 (which may function as recording electrodes or ablation electrodes), electrode wires 20, pull wires 22, and any other device components. As a non-limiting example, each electrode 18 may consist of a rounded portion 24 (for example, having a substantially hemispherical shape), a neck portion 26, and a shoulder portion 28 (such as described in more detail in FIGS. 4 and 5.

Figure 3:
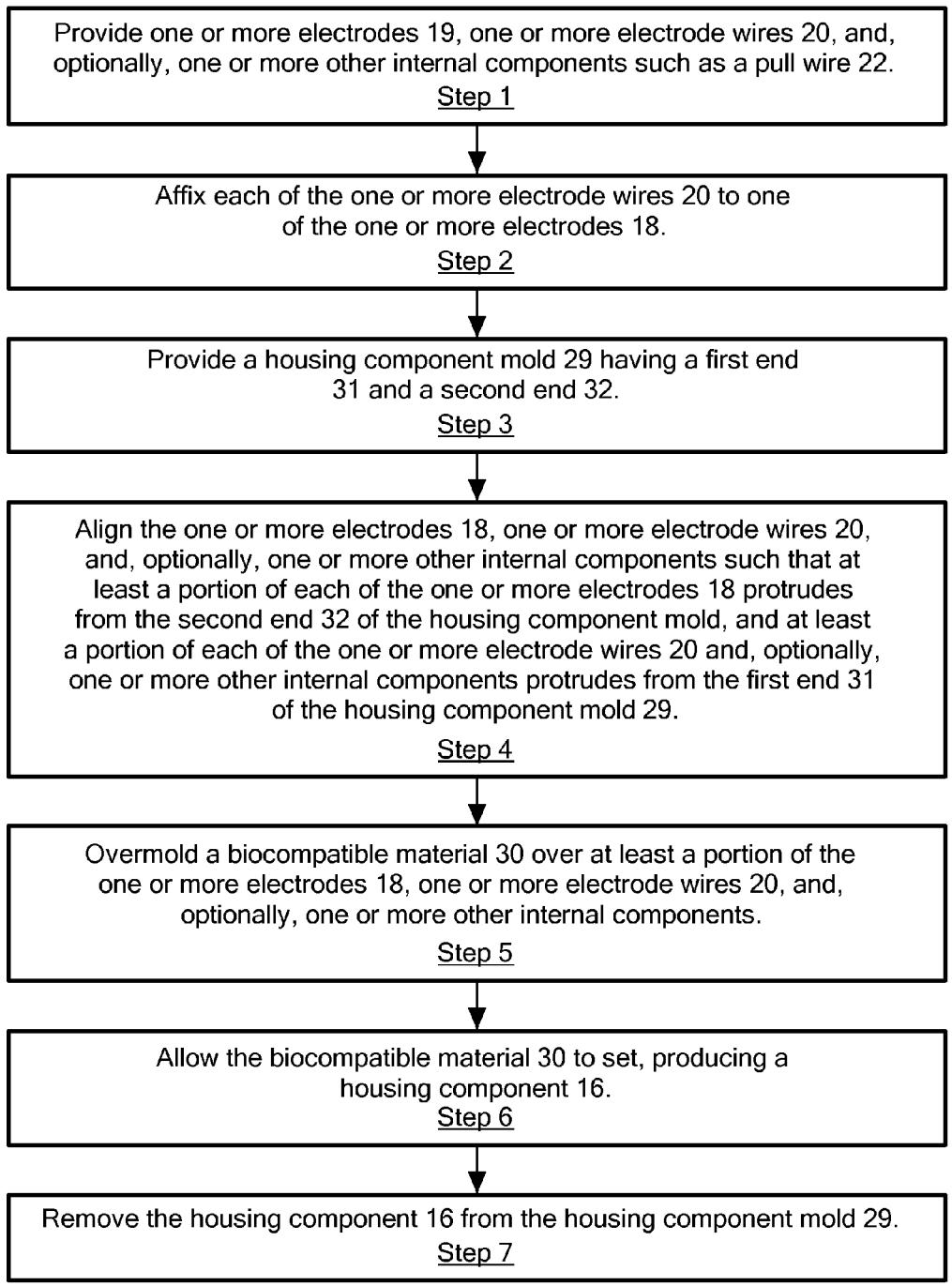
FIG. 3 shows a flow chart of a first method for manufacturing a distal portion of a medical device having a dome component portion and insulation component portion combined into a housing component.

Referring now to FIG. 3, a flow chart of a method for manufacturing a distal portion of a medical device having a dome component portion and insulation component portion combined into a housing component is shown. In Step 1, one or more electrodes 18, one or more electrode wires 20, and, optionally, one or more other internal components such as a pull wire 22 are provided. In Step 2, each of the one or more electrode wires 20 is affixed to one of the one or more electrodes 18 (for example, as shown and described in FIGS. 4 and 5). In Step 3, a housing component mold 29 having a first end 31 and a second end 32 is provided. The housing component mold 29 may be sized and configured to produce a housing component 16 as shown, for example, in FIGS. 1 and 2. In Step 4, the one or more electrodes 18, one or more electrode wires 20, and, optionally, one or more other internal components (for example, a pull wire 22) are aligned within the housing component mold 29 such that at least a portion of each of the one or more electrodes 18 protrudes at from the second end 32 of the housing component mold 29, and at least a portion of each of the one or more electrode wires 20 and, optionally, one or more other internal components protrudes from the first end 31 of the housing component mold 29 (as shown in FIG. 6). In Step 5, a biocompatible material 30 (such as PEEK, for example) is overmolded (also known as insert molded) or injection molded over at least a portion of the one or more electrodes 18, one or more electrode wires 20, and, optionally, one or more other internal components. In Step 6, the biocompatible material 30 is allowed to set, cool, or cure, thereby forming a housing component 16. In Step 7, the housing component 16 is removed from the housing component mold 29. The resulting housing component 16 may have a distal portion 33 and a proximal portion 34. The distal portion 33 of the housing component 16 may house the one or more electrodes 18, whereas the proximal portion 34 of the housing component 16 may later be affixed to body of a medical device, such as an elongate body of a mapping and/or ablation catheter.

Figure 4:
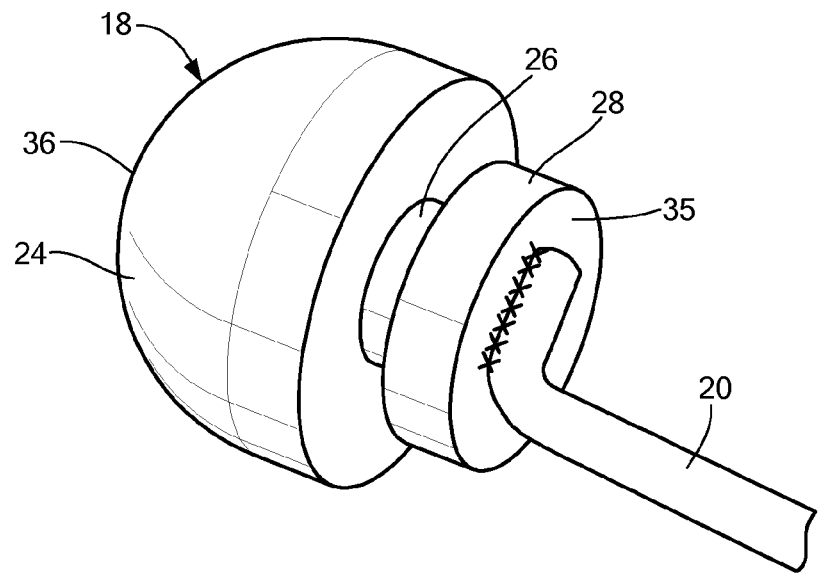
FIG. 4 shows a first embodiment of a recording electrode.

Referring now to FIG. 4, a first embodiment of a recording or ablation electrode is shown. The electrode 18 shown in FIG. 4 includes a rounded head portion 24 (for example, having a substantially hemispherical shape), a neck portion 26, and a flattened shoulder portion 28. The electrode may have a proximal portion 35 and a distal portion 36. The flattened shape of the shoulder portion 28 is located at the proximal portion 35 of the electrode 18 and provides a point of attachment for the electrode wire 20. For example, the wire 20 may be laser welded or resistance-welded to the proximal portion 35 of the electrode 18 at the flat surface of the shoulder portion 28, as depicted by hash marks in FIG. 4. The neck portion 26 of the electrode 18 has a diameter that is narrower than that of both the rounded head portion 24 and shoulder portion 28. As a non-limiting example, the diameter of the rounded head portion 24 may be approximately 0.035 inch and the diameter of the shoulder portion 28 may be approximately 0.024 inch, whereas the diameter of the neck portion 26 may be approximately 0.020 inch. During the overmolding or injection molding process, biocompatible material will flow into the recessed area created by the neck portion 26, thereby providing increased surface area for the biocompatible material and creating a stronger bond between the electrode 18 and housing component 16.

Figure 5:
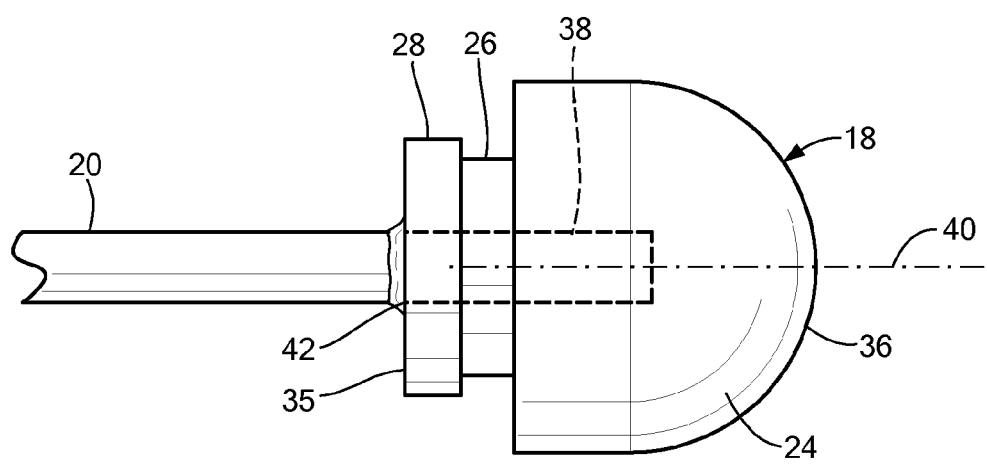
FIG. 5 shows a second embodiment of a recording electrode.
Figure 6:
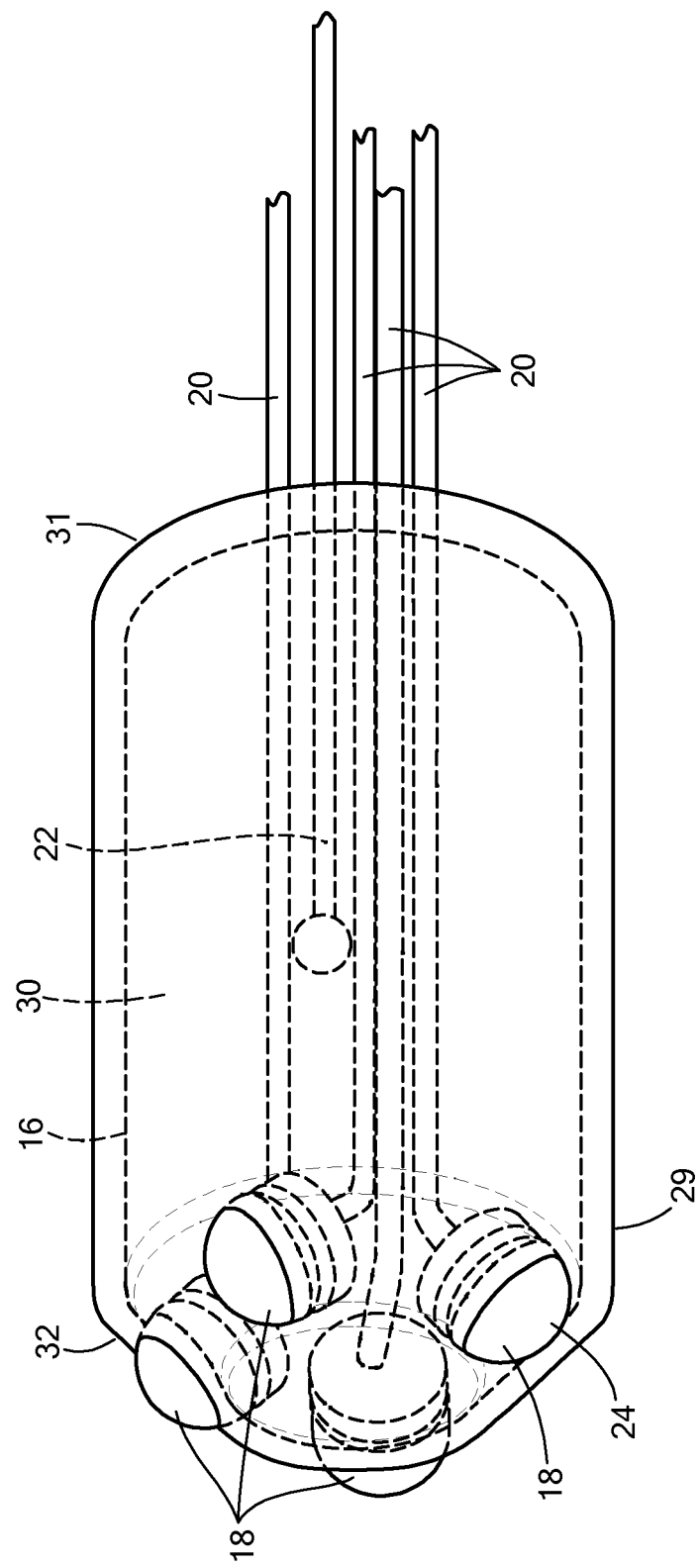
FIG. 6 shows a simplified view of a housing component within a housing mold.

Referring now to FIG. 5, a second embodiment of a recording or ablation electrode is shown. The electrode 18 is substantially similar to that shown and described in FIG. 4, except that the electrode 18 of FIG. 5 further includes a substantially cylindrical recess 38 that is coaxial to the longitudinal axis 40 of the electrode 18. As a non-limiting example, the recess 38 may have a diameter of approximately 0.008 inch and a depth of approximately 0.020 inch. The mouth or opening 42 of the recess 38 may be located on the flat, shoulder portion 28 on the proximal portion 35 of the electrode 18, and the recess 38 may extend from the shoulder portion 28 into the rounded head portion 24 of the electrode 18. When attaching the electrode 18 to an electrode wire 20, the electrode wire 20 may be inserted into and soldered or welded to the recess 38 of the electrode 18 in any suitable manner. Thus, proper alignment between the electrode 18 and electrode wire 20 is greatly facilitated.

Referring now to FIG. 6, a simplified view of a housing component within a housing mold is shown. As described in FIG. 3, the one or more electrodes 18, one or more electrode wires 20, and, optionally, one or more other internal components (for example, a pull wire 22) are aligned within the housing component mold 29 such that at least a portion of each of the one or more electrodes 18 protrudes at from the second end 32 of the housing component mold 29, and at least a portion of each of the one or more electrode wires 20 and, optionally, one or more other internal components protrudes from the first end 31 of the housing component mold 29 (as shown in FIG. 6). For example, at least a portion of the electrode rounded head 24 may protrude from the housing component mold 29, whereas the neck portion 26 and shoulder portion 28 of the electrode 18 may be within the housing component mold 29. However, any size, shape, or configuration of electrode may be used, and the electrode is not limited to that as shown and described in FIGS. 4 and 5. Further, the electrode heads 24 may be entirely within the mold 29, but only a portion of the electrode heads 24 may be overmolded with the biocompatible material 30. The housing component mold 29 shown in FIG. 6 may be greatly simplified, and merely shows that at least a portion of each electrode 18 is not overmolded with biocompatible material 30.

Referring now to FIGS. 7A-7D, a second method of manufacturing a distal portion of a medical device having a housing component that is overmolded onto electrode wires is shown. Like the housing components 16 of FIGS. 1 and 2 and the method of FIG. 3, the housing component 16 of FIGS. 7A-7D may be overmolded onto one or more electrode wires 20. However, the medical device distal portion 10 shown in FIG. 7C does not include the ball electrodes 18 shown and described in FIGS. 5 and 6. Rather, the electrodes 18 are formed by sputtering or otherwise depositing an electrically conductive material 44 over at least a portion of the housing component 16, such as rounded or protruding portions 46 of the housing component 16. For example, the first step of the method shown in FIG. 7A, one or more wires 20 composed of an electrically conductive material may be provided. Each wire may have a longitudinal axis 48, a proximal portion 50, and a distal portion 52. Although not shown in FIGS. 7A-7D, additional components may be included, such as one or more pull wires.

Figure 7A:
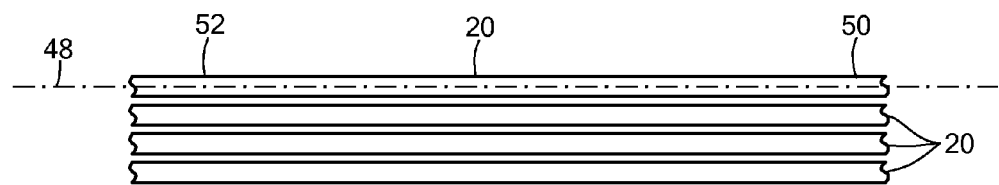
FIGS. 7A-7D show a second method of manufacturing a distal portion of a medical device having a housing component that is overmolded onto electrode wires. The wires are cleaved and sanded at the level of the overmolded material and a thin film of Platinum (or like metal) is deposited onto the rounded protrusions.
Figure 7B:
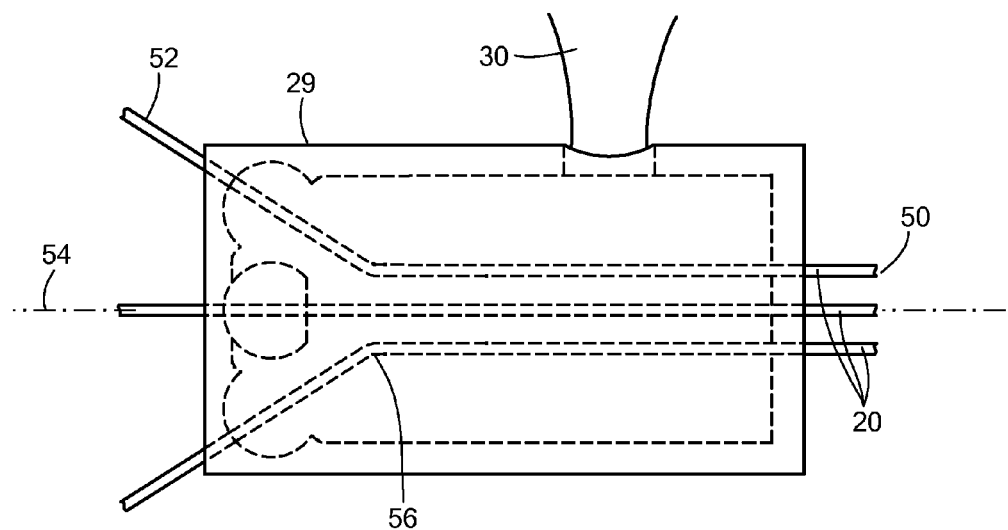
Figure 7C:
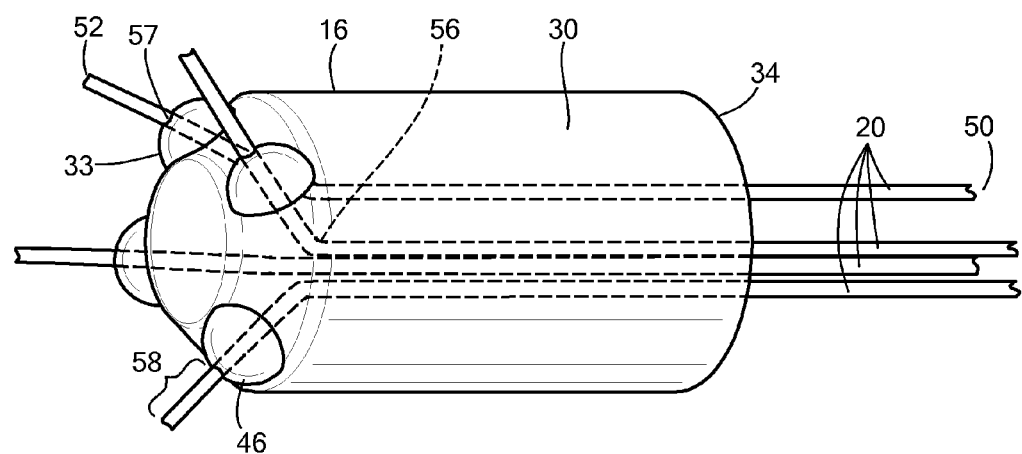
Figure 7D:
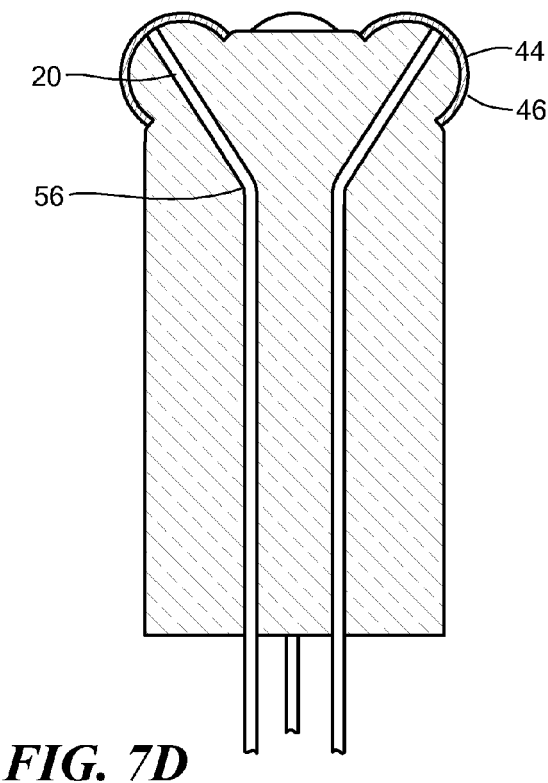

In the second step, generally shown in FIG. 7B, the one or more wires 20 may be aligned within a housing component mold 29. Once the wires 20 are aligned within the housing component mold 29, a biocompatible material 30 (for example, PEEK) may be injected or otherwise introduced into the mold 29, enveloping the wire portions within the housing component mold 29. The biocompatible material 30 is then allowed to cool, cure, and/or set. The housing component mold 29 may be configured to create a housing component 16 as shown in FIG. 1; however, the housing component mold 29 may create a housing component 16 that includes one or more rounded portions 46 (for example, substantially hemispherical protuberances) formed from the biocompatible overmolding material 30, and not a housing component 16 in which one or more spherical electrodes 18 are affixed. Further, the one or more wires 20 may be aligned along a housing component central axis 54, and the distal portion 52 of each of the wires 20 may protrude beyond a first end 31 of the mold and a proximal portion 50 of each of the wires 20 may protrude beyond a second end 32 of the mold 29 (as shown in FIG. 7B). The distal portion 52 of each of the wires 20 may be bent at an off-axis angle 56. As shown in FIGS. 7B-7D, this bend 56 allows the wire 20 to exit the housing component 16 at a point 57 that is substantially at the center of the rounded portion 46 (for example, a substantially hemispherical protuberance). Once the biocompatible material 30 has been allowed to cool and/or set, the mold 29 may be removed from the resulting housing component 16.

After the overmolding process is complete, the protruding portion 58 of each wire 20 may be cleaved off at the surface of the housing component 16, leaving a cross-section of each electrode wire 20 exposed at the surface of the housing component 16. The exposed portion of each electrode wire may then be sanded to create a smooth surface of the housing component 16. Then, a mask or similar device may be placed in contact with the distal portion 33 of the housing component 16 so that only the rounded or hemispherical portions 46 (or other surface area portions containing the exposed cross-section of electrode wire) are unmasked. A material such as platinum-iridium (Pt—Ir) or other conductive material 44 may then be deposited on the exposed or unmasked areas to create a thin conductive layer 44 in contact with the electrode wire 20. This simplified electrode is not only less expensive to manufacture than traditional electrodes, but also involves minimal alignment within the housing component.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of manufacturing a distal portion of a medical device comprising:

providing an electrode and an electrode wire, the electrode wire having a longitudinal axis, a proximal portion, and a distal portion including a distalmost end;

affixing the distalmost end of the electrode wire to the electrode;

bending the distal portion of the electrode wire to create an off-axis portion that extends at an angle away from the longitudinal axis of the electrode wire and includes the distalmost end of the electrode wire;

providing a housing component mold defining a first end and a second end opposite the first end;

aligning within the housing component mold the electrode and electrode wire having the off-axis bend such that at least a portion of the electrode protrudes from the second end of the housing component mold at a point that is off-center from the longitudinal axis of the electrode wire and at least a portion of the proximal portion of the electrode wire protrudes from the first end of the housing component mold;

introducing a biocompatible material into the housing component mold;

allowing the biocompatible material to set, creating a housing component; and removing the housing component from the housing component mold, the housing component both rigidly encapsulating and insulating the electrode.

2. The method of claim 1, wherein the electrode defines a first end, a second end opposite the first end, a rounded head portion at the first end, a shoulder portion at the second end, and a neck portion between the head portion and the shoulder portion, the shoulder portion defining at least one flat surface.

3. The method of claim 2, wherein the electrode further defines a proximal face at the second end, the at least one flat surface of the shoulder portion including a flat surface at the proximal face.

4. The method of claim 3, wherein the neck portion has a diameter that is less than the diameter of each of the rounded head portion and the shoulder portion.

5. The method of claim 4, wherein affixing the electrode wire to the electrode comprises affixing the distalmost end of the electrode wire to the flat surface at the proximal portion of the electrode.

6. The method of claim 4, wherein the electrode further defines a longitudinal axis and a recess that is coaxial with the longitudinal axis of the electrode.

7. The method of claim 6, wherein the off-axis portion of the electrode wire defines a longitudinal axis that is different than the longitudinal axis of the electrode wire, affixing the electrode wire to the electrode comprising inserting the distalmost end of the electrode wire into the recess in the electrode, the longitudinal axis of the electrode and the longitudinal axis of the longitudinal axis of the off-axis portion of the electrode wire being substantially coaxial.

8. The method of claim 2, wherein at least a portion of the rounded head portion of the electrode protrudes from the housing component.

9. The method of claim 1, wherein the biocompatible material is at least one of polyetheretherketone (PEEK), polyurethane, or polyetherimide.

10. The method of claim 1, further comprising aligning a pull wire within the housing component mold, the pull wire having a proximal portion and a distal portion, such that the proximal portion of the pull wire protrudes from the second end of the housing component mold and the distal portion is entirely within the housing component mold.

* * * * *